(12) United States Patent
Markert et al.

(10) Patent No.: US 6,933,270 B2
(45) Date of Patent: Aug. 23, 2005

(54) 3,3-DIMETHYLCYCLOHEXANE DERIVATIVES

(75) Inventors: Thomas Markert, Monheim (DE); Ralph Nemitz, Juechen (DE); Theo Ten Pierik, Venlo (NL)

(73) Assignee: Kao Corporation, Tokyo (JP)

( * ) Notice: Subject to any disclaimer, the term of this patent is extended or adjusted under 35 U.S.C. 154(b) by 244 days.

(21) Appl. No.: 10/276,941

(22) PCT Filed: Apr. 28, 2001

(86) PCT No.: PCT/EP01/04820

§ 371 (c)(1),
(2), (4) Date: Nov. 21, 2002

(87) PCT Pub. No.: WO01/90038

PCT Pub. Date: Nov. 29, 2001

(65) Prior Publication Data

US 2003/0148919 A1 Aug. 7, 2003

(30) Foreign Application Priority Data

May 25, 2000 (DE) ......................... 100 26 004

(51) Int. Cl.⁷ ............................................ A61K 7/46
(52) U.S. Cl. ............................. 512/27; 512/26; 512/8; 512/25; 568/420
(58) Field of Search ........................... 568/420; 512/27, 512/8, 25, 26

(56) References Cited

U.S. PATENT DOCUMENTS 6,451,758 B1 * 9/2002 Markert et al. ............... 512/27

FOREIGN PATENT DOCUMENTS

CH          678 424 A     9/1991
JP          04 021649 A   1/1992

* cited by examiner

*Primary Examiner*—Monique T. Cole
(74) *Attorney, Agent, or Firm*—Oblon, Spivak, McClelland, Maier & Neustadt, P.C.

(57) ABSTRACT

Compounds of the formula (I):

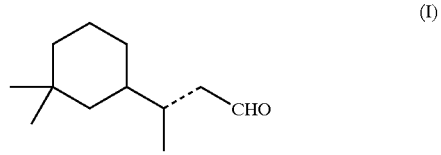

wherein the bond between the α- and β-positions to the aldehyde group represents a C—C single bond or a cis- or trans-configured C═C double bond are useful as perfumes and perfume ingredients.

3 Claims, No Drawings

3,3-DIMETHYLCYCLOHEXANE DERIVATIVES

BACKGROUND OF THE INVENTION

This invention relates to new 3,3-dimethylcyclohexane derivatives and to their use as perfumes.

PRIOR ART

Judging by demand, many natural perfumes are available in totally inadequate quantities. For example, 5,000 kg of rose blossoms are required to produce 1 kg of rose oil. The consequences are extremely limited annual world production and a high price. Accordingly, it is clear that there is a constant need in the perfume industry for new perfumes with interesting fragrance notes. On the one hand, the range of naturally available perfumes can be extended in this way; on the other hand, it is thus possible to make the necessary adaptations to changing fashion trends. In addition, it is possible in this way to meet the steadily increasing demand for odor enhancers for products of everyday use, such as cosmetics and cleaners.

In addition, there is generally a constant need for synthetic perfumes which can be favorably produced in a consistent quality and which have desirable olfactory properties, i.e. in particular pleasant, near-natural and qualitatively new odor profiles of adequate intensity, and which are capable of advantageously influencing the fragrance of cosmetic and consumer products. In other words, there is a constant need for compounds which have characteristic new odor profiles coupled with high staying power, intensity of odor and emanative power.

DESCRIPTION OF THE INVENTION

It has been found that the compounds corresponding to general formula (I) excellently satisfy the above-mentioned requirements in every respect and may advantageously be used as perfumes with differently nuanced perfume notes characterized by high staying power.

In a first embodiment, the present invention relates to 3,3-dimethylcyclohexane derivatives corresponding to general formula (I):

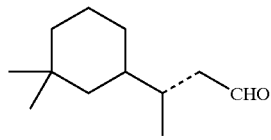

(I)

in which the chain line connecting the carbon atoms in the α- and β-positions to the aldehyde group represents a C—C single bond or a cis- or trans-configured C=C double bond.

In another embodiment, the present invention relates to the use of 3,3-dimethylcyclohexane derivatives corresponding to general formula (I) above as perfumes. The compounds may be used both individually and in combination with one another.

The compounds (I) according to the invention are distinguished by an odor characteristic in which fruity and woody notes and ionone aspects dominate. They show excellent stability in cosmetic and consumer perfumery formulations.

The compounds (I) may be prepared by known synthesis processes of organic chemistry.

In perfume compositions, the compounds (I) strengthen harmony, emanation, naturalness and also staying power, the quantities used being adapted to the particular perfume note required taking the other ingredients of the composition into account.

The fact that the compounds (I) have the above-mentioned perfume notes was not foreseeable and, hence, is further confirmation of the general experience that the olfactory properties of known perfumes do not allow any definitive conclusions to be drawn as to the properties of structurally related compounds because neither the mechanism of odor perception nor the influence of chemical structure on odor perception has been sufficiently researched, so that it is not normally possible to predict whether modifications to the structure of known perfumes will in fact lead to changes in their olfactory properties or whether these changes will be positive or negative.

By virtue of their odor profile, the compounds corresponding to formula (I) are also particularly suitable for modifying and enhancing known compositions. Particular emphasis is placed on their extreme intensity of odor which contributes quite generally towards refining the composition.

The compounds corresponding to formula (I) may be combined with many known perfume ingredients, for example other perfumes of natural, synthetic or partly synthetic origin, essential oils and plant extracts. The range of natural fragrances can thus include both high-volatility and also medium-volatility and low-volatility components while the range of synthetic perfumes may include representatives of virtually every class of compounds.

Examples of suitable substances with which the compounds (I) may be combined are, in particular,
(a) natural products, such as tree moss absolue, basil oil, citrus oils, such as bergamot oil, mandarin oil, etc., mastix absolue, myrtle oil, palmarosa oil, patchouli oil, petitgrain oil, wormwood oil, myrrh oil, olibanum oil
(b) alcohols, such as farnesol, geraniol, linalool, nerol, phenylethyl alcohol, rhodinol, cinnamic alcohol, sandalore [3-methyl-5-(2,2,3-trimethylcyclopent-3-en-1-yl)-pentan-2-ol], sandela [3-isocamphyl-(5)-cyclohexanol]
(c) aldehydes, such as citral, Helional®, α-hexyl cinnamaldehyde, hydroxycitronellal, Lilial® [p-tert.butyl-α-methyldihydrocinnamalde-hyde], methylnonyl acetaldehyde
(d) ketones, such as allylionone, α-ionone, β-ionone, isoraldein, methyl ionone
(e) esters, such as allylphenoxyacetate, benzyl salicylate, cinnamyl propionate, citronellyl acetate, decyl acetate, dimethylbenzyl carbinyl acetate, ethyl acetoacetate, hexenyl isobutyrate, linalyl acetate, methyl dihydrojasmonate, vetiveryl acetate, cyclohexyl salicylate
(f) lactones, such as gamma-undecalactone, 1-oxaspiro[4.4]-nonan-2-one
and various other components often used in perfumery, such as musk and sandalwood perfumes, indole, p-methan-8-thiol-3-one, methyl eugenol, Ambroxan.

It is also remarkable how the compounds corresponding to formula (I) round off and harmonize the odor notes of a broad range of known compositions without unpleasantly dominating them in any way. 3-(3,3-dimethylcyclohex-1-yl)-butanal is particularly emphasized in this regard.

The compounds according to the invention or mixtures thereof may be used in perfume compositions in quantities of 1 to 70% by weight, based on the mixture as a whole. Mixtures of compounds (I) according to the invention and compositions of this type may be used both for perfuming cosmetic preparations, such as lotions, creams, shampoos, soaps, ointments, powders, aerosols, toothpastes, mouthwashes, deodorants, and also in alcohol-based perfumery (for example colognes, toilet waters, extracts). The compounds according to the invention or mixtures thereof may also be used for perfuming commercial products, such as detergents, fabric softeners and textile treatment preparations. For perfuming these various products, the compositions are added in an olfactorily effective quantity, more particularly in a concentration of 0.05 to 2% by weight, based on the product as a whole. However, these values are not intended to represent limits because the experienced perfumer can also obtain effects with even lower concentrations or can build up new complexes with even higher doses.

EXAMPLES

Preparation Procedure:

Example 1

Preparation of 1,1-diethoxy-1-(3,3-dimethylcyclohex-1-yl)-ethane

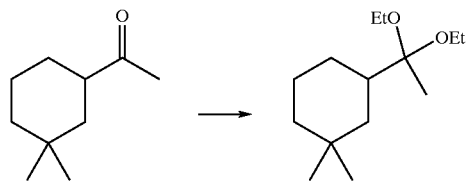

Materials:
1) 154.0 g (1 mol) 1-(3,3-dimethylcyclohex-1-yl)-ethanone
2) 177,8 g (1.2 mol) triethylorthoformate
3) 0.1874 g potassium hydrogen sulfate
4) 600 ml ethanol Apparatus:
Two-liter three-necked flask, stirrer, thermometer, drying tube (Blaugel [blue gel])

Procedure:
Components 1), 2), 3) and 4) were successively introduced into the reaction flask and stirred for 24 hours at room temperature in the absence of moisture. The course of the reaction was monitored by gas chromatography (GC). 76% of product had formed after 24 hours. After stirring for another 7 hours, hardly any further conversion could be detected. The reaction was neutralized by addition of 2 ml of sodium methanolate solution (30% in methanol). Excess ethanol and the formic acid ethyl ester formed were distilled off in a water jet vacuum in a rotary evaporator. The crude diethyl ketal of the 1-(3,3-dimethylcyclohex-1-yl)-ethanone was distilled in a 30 cm packed column. The main fraction had a GC purity of 78% and distilled over at boiling temperatures of 70–72°/0.1 mbar.

Yield:
51% of the theoretical.

Analysis:
The $^1$H-NMR spectrum (280 MHz, CDCl$_3$) showed 2 singlets for the geminal methyl groups on the cyclohexane ring at 0.9 ppm (6 H) and 2 triplets and 1 singlet at 1.2 ppm for the remaining three methyl groups (9 H). The 2 methylene groups of the ethoxy radicals produced 2 quadruplets at 3,4 ppm which were superposed on one another (4H) and the 4 methylene groups of the cyclohexane ring showed several partly split and broadened signals over a range from 0.7 to 2.0 ppm (8 H). The single proton of the CH group also fell into this range and was presumably among the methyl group signals at 1.2 ppm.

Odor Characteristic:
Initial perfume fruity, currant, damascone, reminiscent of the Cognis perfumes Floramat® and Jasmacyclat®. No discernible after-smell after 24 hours on a test strip.

Example 2

Preparation of 1,1,3-triethoxy-3-(3,3-dimethylcyclohex-1-yl)-butane

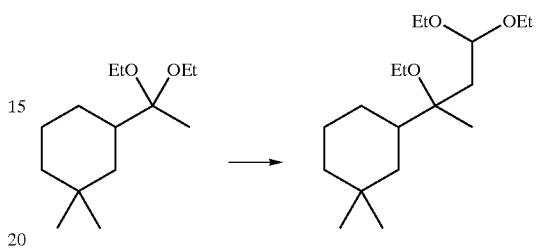

Materials:
1) 104.3 g (0.46 mol) 1,1-diethoxy-1-(3,3-dimethylcyclohex-1-yl)-ethane prepared in accordance with Example 1
2) 36.6 ml zinc chloride solution (10% in ethyl acetate)
3) 48.0 ml (0.5 mol) ethyl vinyl ether (Acros)

Apparatus:
500 ml three-necked flask with stirrer, thermometer, reflux condenser and dropping funnel Procedure:
Components 1) and 2) were successively weighed into the reaction flask and heated with stirring to 50° C. Component 3) was continuously added with stirring over a period of 0.5 hour. The temperature of the mixture rose to 53° C. The mixture was then stirred for 3 hours at 48° C. Monitoring of the conversion showed that the educt had reacted off completely, the main component making up 49%.

Working Up:
The reaction mixture was transferred to a separation funnel and washed until neutral with water and sodium hydrogen carbonate solution. The organic phase was dried over sodium sulfate and concentrated in a rotary evaporator. 125 g crude product were distilled in a 30 cm packed column.

The main fraction contained 71.2 g 1,1,3-triethoxy-3-(3,3-dimethylcyclohex-1-yl)-butane (boiling point 96–108° C./0.08 mbar, GC purity 97.8%).

Yield:
56% of the theoretical.

Analysis:
The $^1$H-NMR spectrum (in CDCl$_3$, 280 MHz) showed the 2 geminal methyl groups as pseudosinglets at 0.9 ppm, 1 methyl group as 2 singlets at 1.1 ppm and the 3 methyl groups of the ethoxy radicals as triplets at 1.1 and 1.2 ppm. The 4 methylene groups of the cyclohexane ring appeared as very broad signals between 0.8 and 1.8 ppm. The 3 methylene groups of ethoxy radicals produced quadruplets at 3.3; 3.5 and 3.6 ppm. The methylene group of the side chain showed 2 superposed doublets at 1.8 ppm. The acetal proton produced 2 triplets at 4.7 ppm.

Odor Characteristic:
Initial perfume fruity, rum aroma, alcohlic, Grappa note. No perceptible odor after 24 hours on the test strip.

Example 3

Preparation of 3-(3,3-Dimethylcyclohex-1-yl)-but-2-en-1-al

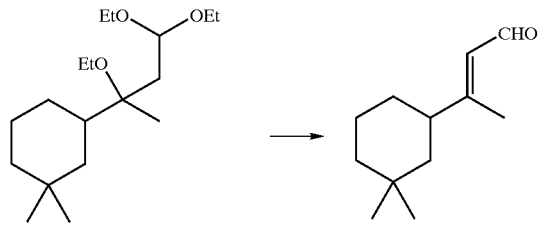

Materials:
1) 65.2 g (0.22 mol) 1,1,3-triethoxy-3-(3,3-dimethylcyclohex-1-yl)-butane (prepared in accordance with Example 2)
2) 287.9 g glacial acetic acid (Riedel de Haan)
3) 30.1 g sodium acetate
4) 20.2 g water Apparatus:
1-liter stirred reactor with thermometer and reflux condenser Procedure:
Components 1), 2), 3) and 4) were introduced into the reactor and stirred for 5 hours at 90° C. The reaction mixture was left overnight to cool to room temperature. The GC of the organic phase showed complete conversion.

Working Up:
The mixture was poured onto ice and neutralized, the organic phase was removed and the water phase was extracted with ether. The organic phases were dried over sodium sulfate and concentrated in a rotary evaporator.

29.2 g residue were distilled in a 30 cm packed column. 20.5 g main fraction distilling over at boiling temperatures of 70–72°/0.06 mbar was isolated (GC purity 97%).

Analysis:
The $^1$H-NMR spectrum (400 MHz, in CDCl$_3$) was very complex and is interpreted as follows: 1 singlet at 0.9 ppm stands for the two geminal methyl groups on the cyclohexane ring. Since this signal has the non-assignable forest of signals between 0.8 and 1.8 ppm underneath, it is only possible to integrate the entire range up to 2.3 ppm which corresponds to slightly more than the 18 expected protons. Two similar-looking, slightly split singlets are conspicuous at 1.9 and 2.2 ppm; integration points to 3 protons of which 15% belongs to the signal at 1.9 ppm and 85% to the signal at 2.2 ppm. A main component and a secondary component are clearly present in the mixture. The two signals are assigned to the methyl group of the side chain. The split seems to correlate with the split of the olefinic proton, main component at 5.9 ppm, to a pseudotriplet of the doublet. The doublet split of the olefinic proton shows the same coupling constant as the aldehyde proton at 10.0 ppm. A secondary component is discernible with a weak signal for the olefinic proton at 5.8 ppm and the aldehyde proton at 10.05 ppm.

Odor Characteristic:
Initial perfume green, dry, dusty, fruity, cassis, ionone, wood. After 24 hours on the test strip, after-small fresh, fruity, woody

Example 4

Preparation of 3-(3,3-dimethylcyclohex-1-yl)-butanal

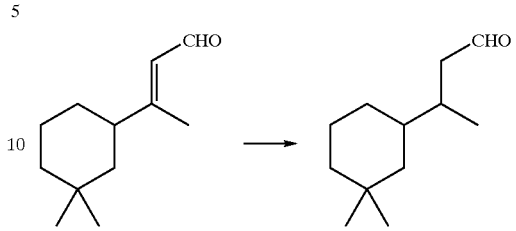

Materials:
1) 18.0 g (0.1 mol) 3-(3,3-dimethylcyclohex-1-yl)-but-2-en-1-al prepared in accordance with Example 3
2) 0.1 g RCh-Katalysator (catalyst) 50/8 (Hoechst) 5% Pd/C (RCh is short for "Ruhrchemie")
3) 100 ml cyclohexane Apparatus:
High-pressure steel autoclave Procedure:
Components 1), 2) and 3) were successively weighed into the autoclave insert and then hydrogenated with stirring for 7 hours at 70° C./20 bar hydrogen excess pressure.

Working Up:
After cooling and venting, the catalyst was filtered off and the reaction mixture was concentrated in a rotary evaporator. 14.5 g of residue were distilled in a 30 cm packed column. Product fractions with a 3-(3,3-dimethyclychex-1-yl)-butanal content corresponding to more than 90% (GC measurement) were obtained at boiling temperatures of 53–55° C./0.06 mbar.

Analysis:
The $^1$H-NMR spectrum (280 MHz, in CDCl$_3$) showed 2 singlets and 1 doublet of the 3 methyl groups (9 H) at 0.9 ppm. The 4 CH$_2$ groups of the cyclohexane ring appeared in the range between 1.2 and 2.0 ppm while the signals for the two single protons were presumably in the range from 0.8 to 1.2 ppm and were partly concealed by the signals for the methyl groups. The CH$_2$ group adjacent the aldehyde group showed two degenerated ddd or ddt signals at 2.2 and 2.5 ppm which had the same coupling constants as the dd aldehyde proton signal at 9.8 ppm.

Odor Characteristic:
Initial perfume green, fresh, dry, aldehydic, flowery, emanative; after-smell after 24 hours on the test strip emanative, dry, woody, fruity.

What is claimed is:
1. A compound of the formula (I):

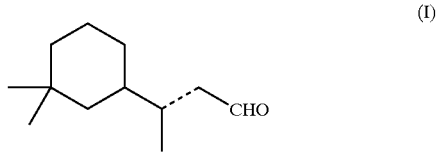

(I)

wherein the bond between the α- and β-positions to the aldehyde group represents a C—C single bond or a cis- or trans-configured C═C double bond.

2. A perfume composition comprising a compound of the formula (I):

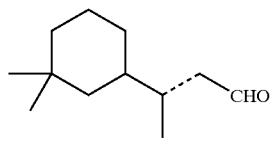
(I)
wherein the bond between the α- and β-positions to the aldehyde group represents a C—C single bond or a cis- or trans-configured C=C double bond.
3. The perfume composition of claim 2 wherein the amount of the compound of formula I in the composition is from 1% to 70% by weight, based on the composition as a whole.
* * * * *